(12) United States Patent
Buchwald et al.

(10) Patent No.: US 6,888,029 B2
(45) Date of Patent: May 3, 2005

(54) TRANSITION-METAL-CATALYZED CARBON-NITROGEN BOND-FORMING METHODS USING CARBENE LIGANDS

(75) Inventors: Stephen L. Buchwald, Newton, MA (US); Joseph M. Fox, Wilmington, DE (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 10/349,198

(22) Filed: Jan. 22, 2003

(65) Prior Publication Data

US 2004/0044250 A1 Mar. 4, 2004

Related U.S. Application Data

(60) Provisional application No. 60/354,321, filed on Feb. 4, 2002.

(51) Int. Cl.[7] ..................... C07C 209/08; C07C 209/10; C07C 209/22
(52) U.S. Cl. ..................... 564/396; 564/405; 564/406; 564/413
(58) Field of Search ................................. 564/396, 405, 564/406, 413

(56) References Cited

FOREIGN PATENT DOCUMENTS

| WO | WO 97/34875 | 9/1997 |
|---|---|---|
| WO | WO 01/66248 A2 | 9/2001 |

OTHER PUBLICATIONS

Böhm et al.; "N–Heterocyclic Carbenes Part 26. N–Heterocyclic Carbene Complexes of Palladium (0): Synthesis and Application in the Suzuki Cross–Coupling Reaction", Journal of Organometallic Chemistry, 595: 186–190, (2000).
Cheng and Trudell; "Synthesis of N–Heteroaryl–7–azabicyclo[2.2.1]heptane Derivatives via Palladium– Bissimidazol–2–Ylidene Complex Catalyzed Amination Reactions", Organic Letters, 3(9):1371–1374, (2001).
Gradel et al.; "Nickel–Catalyzed Amination of Aryl Chlorides Using a Dihydroimidazoline Carbene Ligand", Tetrahedron Letters 42:5689–5692, (2001).
Huang and Nolan; "Efficient Cross–Coupling of Aryl Chlorides with Aryl Grignard Reagents (Kumada Reaction)Mediated by a Palladium/Imidazolium Chloride System", J. Am. Chem. Soc. 121:9889–9890. (1999).
Huang et al.; "General and Efficient Catalytic Amination of Aryl Chlorides Using a Palladium/Bulky Nucleophilic Carbene System", Organic Letters, 1(8): 1307–1309, (1999).
Lee and Nolan; "Efficient Cross–Coupling Reactions of Aryl Chlorides and Bromides with Phenyl– or Vinyltrimethoxysilane Mediated by a Palladium/Imidazolium Chlode System", Organic Letters, 2(14):2053–2055, (2000).
Lee and Hartwig; "Improved Catalysts for the Palladium-Catalyzed Synthesis of Oxindoles by Amide α–Arylation. Rate Acceleration, Use of Aryl Chloride Substrates, and a New Carbene Ligand for Asymmetric Transformation", J. Org. Chem, 66: 3402–3415, (2001).
Lee et al.; "Palladium –Catalyzed Synthesis of Arylamines from Aryl Halides and Lithium Bis(trimethylsilyl)amide as an Ammonia Equivalent", Organic Letters, 3(17): 2729–2732, (2001).
Stauffer et al.; "High Turnover Number and Rapid, Room–Temperature Amination of Chloroarenes Using Saturated Carbene Ligands", Organic Letters, 2(10): 1423–1426, (2000).
Viciu et al.; "An Air–Stable Palladium/N–Heterocyclic Carbene complex and Its Reactivity in Aryl Amination", Organic Letters, 4(13): 2229–2231; (2002).
Viciu et al; "Catalytic Dehalogenation of Aryl Halides Mediated by a Palladium/Imidazolium Salt System", Organometallics 20: 3607–3612, (2001).
Ziegler and Heck, "Palladium Catalyzed Vinylic Substitution with Highly Activated Aryl Halides", The Journal of Organic Chemistry, 43(15): 2941–2946, (Jul. 21, 1978).
Grasa et al.; "Amination Reactions of Aryl Halides with Nitrogen–Containing Reagents Mediated by Palladium/Imidazolium Salt Systems", J. Org. Chem. 66: 7729–7737, (2001).
International Search Report Completed on May 9, 2003 and Mailed on Jun. 20, 2003.

*Primary Examiner*—Brian J. Davis
(74) *Attorney, Agent, or Firm*—Dana M. Gordon; Foley Hoag LLP (57) ABSTRACT

The present invention relates to a process for the preparation of N-aryl amine and N-aryl amide compounds. Generally, the process of the present invention involves reacting a compound having a primary or secondary amino or amido group with an arylating compound, in the presence of a weak base and a transition metal catalyst, under reaction conditions effective to form an N-aryl amine or N-aryl amide compound, the transition metal catalyst comprising a Group 8 metal, e.g., Ni, Pd, or Pt, and at least one carbene-containing ligand. Typically, the transition metal catalyst is formed in a preceding step from the conjugate acid form of the carbene ligand, a stoichiometric amount of a strong base, and a Group 8 metal atom or ion.

20 Claims, 2 Drawing Sheets

| | Amine | Aryl halide | Product | % conversion to product/ GC yield (%) |
|---|---|---|---|---|
| 1a 1b | MeO-C6H4-NH2 | 2-NO2-C6H4-Cl | MeO-C6H4-NH-C6H4-NO2 | 98-isolated yield 96-isolated yield (ligand 2) |
| 2 | 2,6-Me2-C6H3-NH2 | 2-NO2-C6H4-Cl | 2,6-Me2-C6H3-NH-C6H4-NO2 | 91-isolated yield |
| 3 | 2,6-Me2-C6H3-NH2 | MeO2C-C6H4-Cl | 2,6-Me2-C6H3-NH-C6H4-CO2Me | 11 |
| 4 | 2-OMe-C6H4-NH2 | 2-NO2-C6H4-Cl | 2-OMe-C6H4-NH-C6H4-NO2 | 82-isolated yield |
| 5 | 2-OMe-C6H4-NH2 | MeO2C-C6H4-Cl | 2-OMe-C6H4-NH-C6H4-CO2Me | 18 |
| 6 | MeO-C6H4-NH2 | t-Bu-C6H4-Br | MeO-C6H4-NH-C6H4-t-Bu | 12 |
| 7 | MeO-C6H4-NH2 | MeO2C-C6H4-Br | MeO-C6H4-NH-C6H4-CO2Me | 12 |
| 8 | hex-NH2 | 2-NO2-C6H4-Cl | 2-NO2-C6H4-N(H)hex | >19 |
| 9 | morpholine | 2-NO2-C6H4-Cl | 2-NO2-C6H4-morpholine | >38 |
| 10 | morpholine | t-Bu-C6H4-Br | t-Bu-C6H4-morpholine | 12 |
| 11 | morpholine | MeO2C-C6H4-Br | MeO2C-C6H4-morpholine | 18 |
| 12 | indole | 2-NO2-C6H4-Cl | N-(2-NO2-C6H4)-indole | >3 |

TRANSITION-METAL-CATALYZED CARBON-NITROGEN BOND-FORMING METHODS USING CARBENE LIGANDS

RELATED APPLICATIONS

This application claims the benefit of priority to U.S. Provisional Patent Application Ser. No. 60/354,321, filed Feb. 4, 2002.

GOVERNMENT SUPPORT

The invention was made with support provided by the National Institutes of Health; therefore, the government has certain rights in the invention.

BACKGROUND OF THE INVENTION

N-Aryl amines and amides are important substructures in natural products and industrial chemicals, such as pharmaceuticals, dyes, and agricultural products. Palladium-catalyzed methods for the N-arylation of amines and amides are now widely-exploited for the synthesis of arylamine and N-arylamide moieties in pharmaceuticals, materials with important electronic properties, and ligands for early metal catalysts. In particular, the palladium-catalyzed reaction of aryl bromides and aryl iodides with primary and secondary amines and amides is a general method employed for the formation of N-aryl amines and N-aryl amides. However, the reaction conditions employed in these palladium-catalyzed reactions are sufficiently harsh, e.g., in terms of reaction time, reaction temperature, or the requirement for the use of strong base, that many functionalized aryl halide or amine or amide reagents are not suitable reactants because their functional groups will undergo undesired reactions, e.g., decomposition, under the reaction conditions. Moreover, aryl chlorides are typically less suitable reactants in these reactions, due to their low reactivity relative to aryl bromides and aryl iodides. Therefore, it would be advantageous to have additional methods for preparing N-aryl amines and N-aryl amides from arylating compounds, such as aryl halides, and amines and amides.

Further, many currently-practiced methods of producing N-aryl compounds are somewhat inefficient or economically unattractive. For example, workers at Tosoh Company reported that catalysts containing the P(t-Bu)$_3$ ligand provided high turnover numbers for the formation of aryl piperazines with excess ligand (4:1 ratio of P(t-Bu)$_3$ to Pd) at 120 C. Nishiyama, N. et al. Tetrahedron Lett. 39:617–620 (1998); and Yamamoto, T. et al. Tetrahedron Lett. 39:2367–2370 (1998). However, the high temperatures required for this reaction scheme make it somewhat unattractive for commercial use. In another example, Hartwig et al. have shown that a sterically hindered alkylphosphine, prepared in one step, allows for room temperature amination of aryl halides, and that another commercially-available, sterically-hindered alkylphosphine allows for the reaction of aryl chlorides with primary alkylamines under mild conditions. Hamann, B. C. and Hartwig, J. F., J. Am. Chem. Soc. 120:7369–7370 (1998). It has also been reported recently that a P,N ligand containing a biphenyl backbone, which is prepared in three steps, generates a catalyst that leads to examples of room temperature amination chemistry with aryl bromides and room temperature Suzuki chemistry with aryl chlorides. Old, D. W. et al. J. Am. Chem. Soc. 120:9722–9723 (1998).

Notably, nucleophilic N-heterocyclic carbenes, i.e., the imidazoline-2-ylidenes (sometimes called imidazol-2-ylidenes) or so-called "phosphine mimics", have attracted considerable attention as possible alternatives to phosphine ligands in homogeneous catalysis. A primary advantage of these ligands is that an excess of the ligand is not required. It appears that these ligands do not dissociate from the metal center, thereby preventing aggregation of the catalyst to yield the bulk metal. Further, these imidazoline-2-ylidene carbenes appear to be more thermally stable than phosphine ligands.

A small number of publications describe the limited use of carbene ligands of this type in palladium-catalyzed reactions of aryl halides with various nucleophiles, e.g., hydride, amines, and metal amides. See Viciu, M. S. et al. Organometallics 2001, 20, 3607–12; Cheng, J. et al. Org. Lett. 2001, 3, 1371–74; Lee, S. et al. Org. Lett. 2001, 3, 2729–32; Stauffer, S. R. et al. Org. Lett. 2000, 2, 1423–26; Huang, J. et al. Org. Lett. 1999, 1, 1307–09; and published PCT application WO 01/66248. Importantly, the various methods disclosed in these publications are of dubious practical synthetic utility because each of them has an absolute requirement for the use of a strong base at an elevated temperature. As outlined above, an absolute requirement for the use of a strong base at an elevated temperature in a palladium-catalyzed arylation reaction limits the set of reactants that may be used in the reaction due to the limited number of functional groups that are robust to withstand the reaction conditions for the necessary period of time.

Accordingly, a need continues to exist for a general and efficient process of synthesizing N-aryl amines and N-aryl amides from readily available arylating compounds and amines and amides. The discovery and implementation of such a method would simplify the preparation of commercially significant organic N-aryl amines and amides, and would also likely enhance the development of novel polymers and pharmacologically active compounds. The methods of the present invention address that need.

SUMMARY OF THE INVENTION

The present invention is directed to a process for the preparation of N-aryl amine and N-aryl amide compounds. The products of the process of the present invention are valuable intermediates and end products in the pharmaceutical and polymer fields. Generally, the process of the present invention involves reacting a compound having a primary or secondary amino or amido group with an arylating compound, in the presence of a weak base and a transition metal catalyst, under reaction conditions effective to form an N-aryl amine or N-aryl amide compound, the transition metal catalyst comprising a Group 8 metal, e.g., Ni, Pd, or Pt, and at least one carbene-containing ligand. Typically, the transition metal catalyst is formed in a preceding step from the conjugate acid form of the carbene ligand, a stoichiometric amount of a strong base, and a Group 8 metal atom or ion.

In other words, this invention provides a process for forming a bond between an sp$^2$-hybridized carbon atom and an sp$^2$-hybridized or sp$^3$-hybridized nitrogen atom. The processes of the present invention make use of N-heterocyclic carbenes as ancillary ligands in couplings of aryl halides, e.g., aryl chlorides, and aryl sulfonates, e.g., aryl triflates, with primary or secondary amines or amides. Preferred N-heterocyclic carbenes are derived from cations A and B, wherein Ar represents independently for each occurrence aryl or heteroaryl; and R represents independently for each occurrence hydrogen, alkyl, aryl, heteroaryl, aralkyl, or heteroaralkyl.

In certain embodiments, the arylating compound is selected from the group consisting of aryl halides, heteroaryl halides, aryl sulfonates, and heteroaryl sulfonates. In certain embodiments, the arylating compound is selected from the group consisting of aryl iodides, aryl bromides, and aryl chlorides. In certain embodiments, the arylating compound is selected from the group consisting of aryl chlorides and aryl bromides.

In certain embodiments, the transition metal catalyst comprises palladium and at least one carbene-containing ligand. In certain embodiments, the transition metal catalyst is prepared by combining palladium, a 1,1,3,3-tetra-substituted-1,3-diazapropene ammonium ion, and a strong base, e.g., an alkoxide. In preferred embodiments, a 1,1,3,3-tetra-substituted-1,3-diazapropene ammonium ion and an alkoxide base are first combined, thereby producing the at least one carbene-containing ligand, followed by addition of palladium to give the transition metal catalyst. As outlined above, Group 8 transition metals other than palladium may form a component of the transition metal catalyst. Further, other cationic compounds, which upon treatment with a base yield a carbene-containing ligand, may be used to prepare a transition metal catalyst useful in the methods of the present invention.

In certain embodiments, the base used in the carbon-nitrogen bond-forming reaction is a phosphate, carbonate, fluoride, tertiary amine, or hydride. In certain embodiments, the base used in the carbon-nitrogen bond-forming reaction is a phosphate. In certain embodiments, the base used in the carbon-nitrogen bond-forming reaction is potassium phosphate.

DETAILED DESCRIPTION OF THE INVENTION

The present invention is directed to a process for the preparation of N-aryl amine and N-aryl amide compounds. The products of the process of the present invention are valuable intermediates and end products in the pharmaceutical and polymer fields. Generally, the process of the present invention involves reacting a compound having a primary or secondary amino or amido group with an arylating compound, in the presence of a weak base and a transition metal catalyst, under reaction conditions effective to form an N-aryl amine or N-aryl amide compound, the transition metal catalyst comprising a Group 8 metal, e.g., Ni, Pd, or Pt, and at least one carbene-containing ligand. Typically, the transition metal catalyst is formed in a preceding step from the conjugate acid form of the carbene ligand, a stoiciometric amount of a strong base, and a Group 8 metal atom or ion.

The methods of the present invention may be used to form a bond between the halogen-bearing or sulfonate-bearing carbon atom of an aryl halide or sulfonate, heteroaryl halide or sulfonate, or vinyl halide or sulfonate, and a nucleophilic nitrogen atom of an amine or amide. Of course, as mentioned supra, the halogen-bearing carbon of the aryl halide, heteroaryl halide, or vinyl halide, or the sulfonate-bearing carbon of the aryl sulfonate, heteroaryl sulfonate, or vinyl sulfonate, and the nucleophilic nitrogen may be part of a single molecule, rendering the bond-formation intramolecular.

In other words, this invention provides a process for forming a bond between an sp$^2$-hybridized carbon atom and an sp$^2$-hybridized or sp$^3$-hybridized nitrogen atom. The processes of the present invention make use of N-heterocyclic carbenes as ancillary ligands in couplings of aryl halides, e.g., aryl chlorides, and aryl sulfonates, e.g., aryl triflates, with primary or secondary amines or amides. Preferred N-heterocyclic carbenes are derived from cations A and B, wherein Ar represents independently for each occurrence aryl or heteroaryl; and R represents independently for each occurrence hydrogen, alkyl, aryl, heteroaryl, aralkyl, or heteroaralkyl.

In certain embodiments, the arylating compound is selected from the group consisting of aryl halides, heteroaryl halides, aryl sulfonates, and heteroaryl sulfonates. In certain embodiments, the arylating compound is selected from the group consisting of aryl iodides, aryl bromides, and aryl chlorides. In certain embodiments, the arylating compound is selected from the group consisting of aryl chlorides and aryl bromides.

In general, the catalysts used in the methods of the present invention consist essentially of a Group 8 atom or ion, and at least one carbene-containing ligand. The Group 8 atom or ion of the catalyst may be derived from any commercially available salt. In preferred embodiments, the Group 8 atom or ion is palladium. The at least one carbene-containing ligand of a catalyst comprises a carbon atom bearing only six valence electrons, wherein said carbon atom interacts with the aforementioned Group 8 atom or ion. Additionally, with respect to asymmetric at least one carbene-containing ligands, the ligand may be provided as a single enantiomer, a mixture of stereoisomers, or a racemic mixture. The Group 8 atom or ion and the at least one carbene-containing ligand of the catalyst of the methods of the present invention may be added to the reaction mixture separately or simultaneously, or they may be added in the form of preformed catalyst complex. Moreover, the identity of the at least one carbene-containing ligand effects various characteristics of the methods of the present invention.

In certain embodiments, the catalyst of a method of the present invention is covalently tethered to a solid support, e.g., a polymer bead or a resin. For example, the at least one carbene-containing ligand of a catalyst of the present invention may be covalently tethered to a solid support, e.g., a Wang resin. Additionally, one or more of the substrates of a method of the present invention may be covalently tethered to a solid support, e.g., a polymer bead or a resin. For example, the ArX substrate of a method of the present invention may be covalently tethered to a solid support, e.g., a Wang resin. Alternatively, the nucleophilic substrate, i.e., the substrate that effectively replaces X in ArX, of a method of the present invention may be covalently tethered to a solid support, e.g., a Wang resin. Further, in certain embodiments, both substrates may be covalently tethered to a solid support. In certain embodiments, one or more of the substrates or the catalyst or any of them are isolated in a semi-permeable membrane, e.g., a dialysis bag. In certain embodiments of this invention, the catalyst, e.g., through the at least one carbene-containing ligand, may be anchored or supported on a catalyst support, including a refractory oxide, such as silica, alumina, titania, or magnesia; or an aluminosilicate clay, or molecular sieve or zeolite; or an organic polymeric resin.

In certain embodiments, the transition metal catalyst comprises palladium and at least one carbene-containing ligand. In certain embodiments, the transition metal catalyst is prepared by combining palladium, a 1,1,3,3-tetra-substituted-1,3-diazapropene ammonium ion, and a strong base, e.g., an alkoxide. In preferred embodiments, a 1,1,3,3-tetra-substituted-1,3-diazapropene ammonium ion and an alkoxide base are first combined, thereby producing the at least one carbene-containing ligand, followed by addition of palladium to give the transition metal catalyst. As outlined above, Group 8 transition metals other than palladium may form a component of the transition metal catalyst. Further, other cationic compounds, which upon treatment with a base yield a carbene-containing ligand, may be used to prepare a transition metal catalyst useful in the methods of the present invention.

The transition metal catalyst comprises at least one metal atom selected from the group consisting of nickel, palladium, and platinum having a formal oxidation state of zero or two, and is sometimes referred to hereinafter as the metal compound. Inorganic salts of nickel, palladium, or platinum that may be used include bromides, chlorides, fluorides, iodides, cyanides, nitrates, sulfides, sulfites, and sulfates. Organic nickel, palladium, or platinum compounds that may be used include complexes and salts such as carboxylates, e.g., acetates or propionates. Suitable nickel compounds include bis(1,5-cyclooctadiene)nickel, nickel acetate, nickel oxalate, nickel phosphate, nickel stearate, nickel acetylacetonate, nickel tetrafluoroborate, nickel thiocyanate, nickel carbonate, and nickel sulfamate. Suitable palladium compounds include $Pd(OAc)_2$, palladium(II) chloride, $Pd(CH_3CN)_4(BF_4)_2$, $PdCl_2(CH_3CN)_2$, $PdCl_2(PhCN)_2$, $PdCl_2(PPh_3)_2$, tris(dibenzylideneacetone)dipalladium(0), and palladium trifluoroacetate. Suitable platinum compounds include platinum acetylacetonate and platinum chloride. Nickel and palladium compounds are preferred; most preferred are compounds of palladium. Palladium compounds such as palladium acetate and tris(dibenzylideneacetone)dipalladium(0) are most preferred.

In certain preferred embodiments, the transition metal catalyst is synthesized first and separately, followed by being employed in the arylation process. Alternatively, the catalyst can be prepared in situ in the arylation reaction mixture. In embodiments employing the latter, i.e., in situ, approach, a Group 8 catalyst precursor compound, e.g., a palladium salt, and the at least one carbene-containing ligand, or a precursor thereof and a stoichiometric amount of a strong base, are independently added to the reaction mixture, wherein formation of the transition metal catalyst occurs in situ. For example, in the presence of the at least one carbene-containing ligand, in situ formation of the transition metal catalyst occurs. Suitable precursor compounds include alkene and diene complexes of the Group 8 metals, preferably di(benzylidene)acetone (dba) complexes of the Group 8 metals or Group 8 carboxylates. Non-limiting examples of suitable catalyst precursor compounds include [bis-di(benzylidene)acetone]palladium (0), tris-[di(benzylidene)acetone]palladium (0), tris-[di(benzylidene) acetone]-dipalladium (0), palladium acetate, and the analogous complexes of nickel and platinum. Further, any of the aforementioned catalyst precursors may include a solvent of crystallization. Group 8 metals supported on carbon, for example, palladium on carbon, may also be employed as a catalyst precursor. Preferably, the catalyst precursor compound is bis-[di(benzylidene)acetone]palladium(0) or tris-[di(benzylidene)acetone]-dipalladium (0).

The quantity of transition metal catalyst which is employed in the process of this invention is any catalytic quantity, i.e., substoichiometric relative to the aryl halide or aryl sulfonate, which promotes the formation of the N-aryl product. Typically, the transition metal catalyst is present in less than about 20 mole percent, based on the number of moles of the aryl halide or aryl sulfonate. Preferably, the quantity of transition metal catalyst is less than about 10 mole percent, and more preferably less than about 5 mole percent, based on the moles of the aryl halide or aryl sulfonate. In certain preferred embodiments, the quantity of transition metal catalyst is about 1 mole percent, based on the moles of the aryl halide or aryl sulfonate.

Notably, the process described herein may be conducted in any conventional reactor designed for catalytic processes. Continuous, semi-continuous, and batch reactors can be employed. If the catalyst is substantially dissolved in the reaction mixture, as in homogeneous processes, then batch reactors, including stirred tank and pressurized autoclaves, can be employed. If the catalyst is anchored to a support and is substantially in a heterogeneous phase, then fixed-bed and fluidized bed reactors can be used. In certain embodiments, the amine or amide, arylating compound, base, and catalyst are mixed in batch, optionally with a solvent, and the resulting mixture is maintained at a temperature and pressure effective to prepare the N-arylated product.

Any solvent can be used in the process of the invention provided that it does not interfere with the formation of the N-aryl amine or N-aryl amide product. Both aprotic and protic solvents and combinations thereof are acceptable. Suitable aprotic solvents include, but are not limited to, aromatic hydrocarbons, such as toluene and xylene, chlorinated aromatic hydrocarbons, such as dichlorobenzene, and ethers, such as tetrahydroturan (THF) and ethylene glycol dimethyl ether (DME). Suitable protic solvents include, but are not limited to, water and aliphatic alcohols, such as ethanol, isopropanol, and cyclohexonol, as well as glycols and other polyols. Polar solvents are preferred. In certain preferred embodiments, the solvent is an ether. Ethers that may be used include, for example, diethyl ether, di-n-propyl ether, diisopropyl ether, tert-butyl ethyl ether, diheptyl ether, 1;3-dioxolane, 1,4-dioxane, tetrahydrofuran, methyl tetrahydrofuran, glyme (the dimethyl ether of ethylene glycol), diglyme (the dimethyl ether of diethylene glycol), and the like. In certain preferred embodiments, the solvent is DME. The amount of solvent which is employed may be any amount, preferably an amount sufficient to solubilize, at least in part, the reactants and base. A suitable quantity of solvent is determined by the specific process conditions and by the skilled artisan.

Generally, the reagents may be mixed together or added to a solvent in any order. Air is preferably removed from the reaction vessel during the course of the reaction, however this step is not always necessary. If it is desirable or necessary to remove air, the solvent and reaction mixture can be sparged with a non-reactive gas, such as nitrogen, helium, or argon, or the reaction may be conducted under anaerobic conditions. The process conditions can be any operable conditions which yield the desired N-aryl product. Beneficially, the reaction conditions for this process are mild. For example, a preferred temperature for the process of the present invention ranges from about ambient temperature to about 150 C, and preferably, from about 90 C to about 110 C. In certain preferred embodiments, the process of the present invention is conducted at about 100 C. The process may be run at sub-atmospheric pressures if necessary, but typically proceeds at about atmospheric pressure.

A wide variety of strong Bronsted bases are suitable for use in first step, i.e., generation of the catalyst comprising the carbene ligand, of the processes of this invention. Alkali metal salts are preferred bases. In certain embodiments, preferred strong Bronsted bases for generating the transition metal catalyst are alkoxides. For example, lithium, sodium and potassium alkoxides. Preferred alkoxide bases include lithium tert-butoxide, sodium tert-butoxide, and potassium tert-butoxide. In certain preferred embodiments, the strong Bronsted base is sodium tert-butoxide. Of course, the choice of the strong Bronsted base will vary with the particular system of aryl halide or pseudohalide and amine or amide involved.

In certain embodiments, the weak base used in the carbon-nitrogen bond-forming reaction, i.e., the second step of the methods of the present invention, is a phosphate, carbonate, bicarbonate, fluoride, tertiary amine, or hydride. In certain embodiments, the weak base used in the carbon-nitrogen bond-forming reaction is a phosphate. In certain embodiments, the weak base used in the carbon-nitrogen bond-forming reaction is potassium phosphate. Because the sole apparent role of the weak base in this step of the methods is to neutralize the strong acid generated in the carbon-nitrogen bond formation, a wide range of Bronsted bases may be used. Generally, any weak Bronsted base may be used in this step of the methods of the present invention. For example, suitable weak bases include KF, NaF, $K_3PO_4$, $K_2CO_3$, $Na_2CO_3$, $Tl_2CO_3$ and $Cs_2CO_3$, or mixtures thereof. In certain embodiments, the weak Bronsted base used will be selected from the group consisting of phosphates, carbonates, and fluorides. In certain embodiments, the weak base is selected from the group consisting of potassium phosphate, potassium carbonate, potassium fluoride, and cesium carbonate.

Typically, there is no need to use large excesses of base in either step of the methods of the present invention. In preferred embodiments, one equivalent of strong base is used relative the precursor of the carbene ligand. In certain embodiments, no more than four equivalents of the weak base are used, relative to the nucleophilic amine or amide. In other embodiments, no more than two equivalents of the weak base are used, relative to the nucleophilic amine or amide. Further, in reactions using the corresponding anion of the nucleophilic amine or amide in place of its conjugate base, there may be no need for additional weak base.

Directly bonded to the aromatic ring(s) of the aryl halide or pseudohalide (e.g., aryl bromide or aryl sulfonate) is at least one halogen atom selected from a chlorine atom, a bromine atom, and an iodine atom, or at least one pseudohalide group. The aryl halide or aryl pseudohalide can have two or more such halogen atoms with an atomic number greater than nine and/or pseudohalide groups, including combinations of halogen atoms and pseudohalide groups. However, when two or more such groups are present, the halogen atoms with an atomic number greater than nine and/or pseudohalide groups should all be different from each other. For example, when two such substituents are present, they may, for example, be a chlorine atom and a bromine atom, or an iodine atom and a tosylate group. It is preferred that there is only one chlorine atom, bromine atom, iodine atom, or pseudohalide group directly bonded to the aryl ring of the aryl halide or pseudohalide. To prevent self-reaction, it is preferred that amino groups are not present on the aryl halide or pseudohalide.

The aryl moiety of the aryl halide or aryl pseudohalide can be monocyclic or polycyclic, e.g., bicyclic. The aryl moiety of the aryl halide or aryl pseudohalide can be "homocyclic", i.e., comprised of a carbon backbone, e.g., benzene, or heterocyclic, e.g., pyridine. Examples of suitable homocyclic aryl moieties include, but are not limited to, benzene, naphthalene, anthracene, phenanthrene, pyrene, biphenyl, acenaphthalene, fluorene, and indene. Heterocyclic aryl moieties that can be used include, for example, furan, thiophene, oxathiolane, thianthrene, isobenzofuran, phenoxathiin, and the like. Nitrogen-containing heterocycles that can be used include, for example, pyridine, indole, isoxazole, and the like. Benzene is a preferred aryl moiety for the aryl halide or pseudohalide.

For the aryl halide or aryl pseudohalide, substituents other than a chlorine atom, a bromine atom, an iodine atom, and/or a pseudohalide group that may be present including, but not limited to, fluorine atoms, nitro groups, hydrocarbyl groups, alkoxy groups, perfluorohydrocarbyl groups, silyl groups, amide groups, nitrile groups, ether groups, ketone groups, and ester groups. When hydrocarbyl groups are present, they are preferably $C_1$ to $C_{18}$ alkyl groups or $C_6$ to $C_{20}$ aryl or arylalkyl (also known as aralkyl) groups. Examples of suitable hydrocarbyl groups are methyl, ethyl, isopropyl, tert-butyl, cyclopentyl, methylcyclohexyl, decyl, phenyl, tolyl, xylyl, benzyl, naphthyl, and tetrahydronaphthyl. Alkoxy group substituents preferably have $C_1$ to $C_6$ alkyl moieties. Some examples of alkoxy groups are methoxy, ethoxy, isopropoxy, methylcyclopentoxy, and cyclohexoxy. Perfluorohydrocarbyl groups include alkyl and aryl perfluorocarbons; suitable perfluorohydrocarbyl groups are, for example, trifluoromethyl, pentafluoroethyl, pentafluorophenyl, and heptafluoronaphthyl. Substituent silyl groups preferably have $C_1$ to $C_{18}$ alkyl groups or $C_6$ to $C_{20}$ aryl or aralkyl groups, and examples include trimethylsilyl, triisopropylsilyl, tert-butyl(dimethyl)silyl, tridecylsilyl, and triphenylsilyl. Of course, the preferred substituents for the aryl halide or aryl pseudohalide will depend on the desired product.

In certain embodiments, a heteroaryl halide or sulfonate is used, wherein its heteroaryl moiety is a radical of an heteroaromatic (single or polycyclic), such as pyrrole, thiophene, thianthrene, furan, pyran, isobenzofuran, chromene, xanthene, phenoxathiin, pyrrole, imidazole, pyrazole, thiazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, perimidine, phenanthroline, phenazine, phenarsazine, phenothiazine, furazan, phenoxazine, pyrrolidine, oxolane, thiolane, oxazole, piperidine, piperazine, morpholine.

In general, suitable aromatic compounds have the formula $Z_p$ArX, wherein Ar is aryl or heteroaryl; and X is a sulfonate or a halogen selected from the group consisting of chlorine, bromine, and iodine. In certain embodiments, X is a halide selected from the group consisting of chlorine, bromine, and iodine. In certain embodiments, X represents a sulfonate moiety. Further, Z represents one or more optional substituents on the aromatic ring, though each occurence of Z (p>1) is independently selected. By way of example only, each incidence of substitution independently can be, as valence and stability permit, a halogen, a lower alkyl, a lower alkenyl, a lower alkynyl, a carbonyl (e.g., an ester, a carboxylate, or a formate), a thiocarbonyl (e.g., a thiolester, a thiolcarboxylate, or a thiolformate), an aldehyde, an amino, an acylamino, an amido, an amidino, a cyano, a nitro, an azido, a sulfonyl, a sulfoxido, a sulfate, a sulfonate, a sulfamoyl, a sulfonamido, a phosphoryl, a phosphonate, a phosphinate, —$(CH_2)_m$—$R_8$, —$(CH_2)_m$—OH, —$(CH_2)_m$—O-lower alkyl, —$(CH_2)_m$—O-lower alkenyl, —$(CH_2)_m$—O—$(CH_2)_n$—$R_8$, —$(CH_2)_m$—SH, —$(CH_2)_m$—S-lower alkyl, —$(CH_2)_m$—S-lower alkenyl, —$(CH_2)_m$—S—$(CH_2)_n$—$R_8$, or protecting groups of the above or a solid or polymeric support; $R_8$ represents a substituted or unsubstituted aryl, aralkyl, cycloalkyl, cycloalkenyl, or heterocycle; and n and m are independently for each occurrence zero or an integer in the range of 1 to 6. When the aryl moiety is phenyl, p is in the range of 0 to 5. For fused rings, where the number of potential substitution sites on the aryl moiety is greater than five, the range defined for p must be adjusted appropriately.

Amines and amides suitable for use in the method of the present invention include primary and secondary amines and amides. The group(s) of the amine or amide may be saturated, unsaturated, branched, straight-chain, cyclic, or aromatic. Heteroatoms, such as oxygen, sulfur, and silicon, and/or functional groups including ethers, esters, and ketones can be present in the group(s) of the amine or amide. For secondary amines, the two groups on a particular amine may be the same or different.

When an aryl moiety is present in the amine or amide, the aryl moiety can be homocyclic or heterocyclic, as described for the aryl halide or aryl pseudohalide. For the amine, the preferred aryl moieties are benzene and naphthalene. Substituents on the aryl ring, again as described for the aryl halide or aryl pseudohalide, can be hydrogen atoms, fluorine atoms, nitro groups, hydrocarbyl groups, alkoxy groups, perfluorohydrocarbyl groups, silyl groups, ether groups, ketone groups, and ester groups. To prevent self-reaction, it is also preferred that chlorine atoms, bromine atoms, iodine atoms, and/or pseudohalide groups are not present on aromatic ring(s) in the amine or amide. In other words, the aromatic rings in the amine or amide are preferably devoid of halogen atoms with an atomic number greater than nine and pseudohalide groups.

Examples of suitable primary amines include, but are not limited to, methylamine, cyclopropylamine, n-butylamine, tert-butylamine, cyclobutylamine, 2-pentylamine, hexylamine, heptylamine, octylamine, 4-methylcyclooctylamine, decylamine, phenylamine (aniline), 2,4,6-trimethylphenylamine (2,4,6-trimethylaniline), and benzylamine. Suitable secondary amines include dimethylamine, ethylmethylamine, diisopropylamine, di-n-butylamine, di-sec-butylamine, dicyclopentylamine, dihexylamine, di(methylcyclohexyl)amine, piperidine, morpholine, (ethyl)(octyl)amine, (nonyl)(n-propyl)amine, didodecylamine, N-methylphenylamine (N-methyl aniline), (methyl)phenylamine, and the like.

Preferred N-heterocyclic carbenes are imidazoline-2-ylidenes of the following formula:

wherein $R^1$ and $R^2$ are independently selected from the group consisting of alkyl, aryl, and heteroaryl; and $R^3$ and $R^4$ are independently selected from the group consisting of hydrogen, alkyl, aryl, heteroaryl, aralkyl, and heteroaralkyl; and imidazolidine-2-ylidenes of the following formula:

wherein $R^1$ and $R^2$ are independently selected from the group consisting of alkyl, aryl, and heteroaryl; and $R^3$ and $R^4$ are independently selected from the group consisting of hydrogen, alkyl, aryl, heteroaryl, aralkyl, and heteroaralkyl.

Preferably, $R^1$ and $R^2$ are sterically bulky groups. Suitable groups include, but are not limited to, isopropyl, sec-butyl, tert-butyl, 2,2-dimethylpropyl (neopentyl), cyclohexyl, norbornyl, adamantyl, tolyl, 3,5-dimethylphenyl, 2,4,6-trimethylphenyl, 2,6-diisopropylphenyl, and triphenylmethyl. Preferred groups are tert-butyl, 2,4,6-trimethylphenyl, 2,6-diisopropylphenyl, 2,4,6-triisopropylphenyl, 2,4,6-triisopropylphenylmethyl, and triphenylmethyl. Particularly preferred for $R^1$ and $R^2$ are 2,4,6-trimethylphenyl, 2,6-diisopropylphenyl, and 2,4,6-triisopropylphenyl groups.

Examples of suitable $R^3$ and $R^4$ groups include hydrogen, alkyl, aryl, heteroaryl, aralkyl, and heteroaralkyl. When hydrocarbyl groups are present, they are preferably $C_1$ to $C_{18}$ alkyl groups or $C_6$ to $C_{20}$ aryl or aralkyl groups. Examples of suitable alkyl groups are methyl, ethyl, isopropyl, tert-butyl, cyclopentyl, methylcyclohexyl, and decyl. Suitable aryl groups include phenyl, tolyl, xylyl, benzyl, naphthyl, and tetrahydronaphthyl. Hydrogen is most preferred for substituents $R^3$ and $R^4$.

Without being bound by a particular theory, it appears from thermochemical studies that the electron-donating ability of many of the imidazoline-2-ylidene carbene ligands is greater than that of tri(cyclohexyl)phosphine, and that the steric demand of these carbene ligands is also greater than that of tri(cyclohexyl)phosphine. Unfortunately, imidazoline-2-ylidene carbenes and imidazolidine-2-ylidene carbenes are considerably less stable to air and moisture than their corresponding protonated imidazolinium and imidazolidinium salts. Thus, a highly preferred embodiment of this invention involves initial generation of the imidazoline-2-ylidene carbene-containing or imidazolidine-2-ylidene carbene-containing catalyst from the corresponding hydrohalide salt, the Group 8 metal atom or ion, and a stoichiometric amount of a strong base; followed by addition of the aryl donor, the amine or amide, and a weak base; followed by heating until the reaction has proceeded to completion. The protonated salts of the imidazoline-2-ylidene carbenes and imidazolidine-2-ylidene carbenes are monoprotonated. Suitable counterions for the protonated salts are virtually limitless, but halides are preferred counterions. The most preferred counterions are chloride and bromide. The hydrohalide salts of the carbene ligands are straightforward to synthesize and are air-stable. While the absence of oxygen is not necessary when using a protonated salt of an imidazoline-2-ylidene carbene or an imidazolidine-2-ylidene carbene, it is preferred. When using a carbene ligand, the exclusion of oxygen is necessary. In any instance where oxygen is excluded, the presence of an inert gas such as nitrogen, helium, or argon is preferred.

The aryl halide or pseudohalide and the amine or amide may be employed in an ideal molar ratio of about 1:1 when using an aryl halide or pseudohalide that has only one halogen atom (other than a fluorine atom) or pseudohalide group; or either reagent may be used in excess. It is preferred to use the amine or amide in an excess such that the molar ratio of aryl halide or pseudohalide to amine or amide is in the range of from about 1:1 to about 1:3 when using an aryl halide or pseudohalide that has only one halogen atom (other than a fluorine atom) or pseudohalide group. When the aryl halide or pseudohalide has more than one halogen atom (other than fluorine) and/or pseudohalide group, reactions may be carried out in sequence. An amine or amide will react first at the site of the more reactive substituent, e.g., at iodine before bromine. Further, reaction at only the site of the more reactive substituent(s) can be performed. In reactions carried out in sequence where the amines or amides are different, each should be added separately. It is preferred to allow one reaction to finish before the addition of the next amine or amide. When different amines or amides are used, it is preferred to use approximately the ideal molar ratio of aryl halide or pseudohalide to amine or amide to minimize the production of undesired side products.

Definitions

For convenience, certain terms employed in the specification, examples, and appended claims are collected here.

The term "nucleophile" is recognized in the art, and as used herein means a chemical moiety having a reactive pair of electrons. Examples of nucleophiles include uncharged compounds such as water, amines, mercaptans and alcohols, and charged moieties such as alkoxides, thiolates, carbanions, and a variety of organic and inorganic anions. Illustrative anionic nucleophiles include simple anions such as hydroxide, azide, cyanide, thiocyanate, acetate, formate or chloroformate, and bisulfite. Organometallic reagents such as organocuprates, organozincs, organolithiums, Grignard reagents, enolates, acetylides, and the like may, under appropriate reaction conditions, be suitable nucleophiles. Hydride may also be a suitable nucleophile when reduction of the substrate is desired.

The term "electrophile" is art-recognized and refers to chemical moieties which can accept a pair of electrons from a nucleophile as defined above. Electrophiles useful in the method of the present invention include cyclic compounds such as epoxides, aziridines, episulfides, cyclic sulfates, carbonates, lactones, lactams and the like. Non-cyclic electrophiles include sulfates, sulfonates (e.g. tosylates), chlorides, bromides, iodides, and the like The terms "electrophilic atom", "electrophilic center" and "reactive center" as used herein refer to the atom of the substrate which is attacked by, and forms a new bond to, the nucleophile. In most (but not all) cases, this will also be the atom from which the leaving group departs.

The term "electron-withdrawing group" is recognized in the art and as used herein means a functionality which draws electrons to itself more than a hydrogen atom would at the same position. Exemplary electron-withdrawing groups include nitro, ketone, aldehyde, sulfonyl, trifluoromethyl, —CN, chloride, and the like. The term "electron-donating group", as used herein, means a functionality which draws electrons to itself less than a hydrogen atom would at the same position. Exemplary electron-donating groups include amino, methoxy, and the like.

The terms "Lewis base" and "Lewis basic" are recognized in the art, and refer to a chemical moiety capable of donating a pair of electrons under certain reaction conditions. Examples of Lewis basic moieties include uncharged compounds such as alcohols, thiols, olefins, and amines, and charged moieties such as alkoxides, thiolates, carbanions, and a variety of other organic anions.

The terms "Lewis acid" and "Lewis acidic" are art-recognized and refer to chemical moieties which can accept a pair of electrons from a Lewis base.

The term "meso compound" is recognized in the art and means a chemical compound which has at least two chiral centers but is achiral due to an internal plane or point of symmetry.

The term "chiral" refers to molecules which have the property of non-superimposability on their mirror image partner, while the term "achiral" refers to molecules which are superimposable on their mirror image partner. A "prochiral molecule" is an achiral molecule which has the potential to be converted to a chiral molecule in a particular process.

The term "pseudohalide group" refers to groups such as p-toluenesulfonate (tosylate), trifluorormethanesulfonate (triflate), methanesulfonate (meslyate), nonaflate (ONf), and aryl diazonium salts, i.e., $ArN_2^+X^\ominus$, wherein $X^\ominus$ is a non-nucleophilic counterion.

The term "stereoisomers" refers to compounds which have identical chemical constitution, but differ with regard to the arrangement of their atoms or groups in space. In particular, the term "enantiomers" refers to two stereoisomers of a compound which are non-superimposable mirror images of one another. The term "diastereomers", on the other hand, refers to the relationship between a pair of stereoisomers that comprise two or more asymmetric centers and are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product. The subject method is said to produce a "stereoselectively-enriched" product (e.g., enantioselectively-enriched or diastereoselectively-enriched) when the yield of a particular stereoisomer of the product is greater by a statistically significant amount relative to the yield of that stereoisomer resulting from the same reaction run in the absence of a chiral catalyst. For example, an enantioselective reaction catalyzed by one of the subject chiral catalysts will yield an e.e. for a particular enantiomer that is larger than the e.e. of the reaction lacking the chiral catalyst.

The term "regioisomers" refers to compounds which have the same molecular formula but differ in the connectivity of the atoms. Accordingly, a "regioselective process" is one which favors the production of a particular regioisomer over others, e.g., the reaction produces a statistically significant preponderance of a certain regioisomer.

The term "reaction product" means a compound which results from the reaction of a nucleophile and a substrate. In general, the term "reaction product" will be used herein to refer to a stable, isolable compound, and not to unstable intermediates or transition states.

The term "substrate" is intended to mean a chemical compound which can react with a nucleophile, or with a ring-expansion reagent, according to the present invention, to yield at least one product having a stereogenic center.

The term "catalytic amount" is recognized in the art and means a substoichiometric amount relative to a reactant.

As discussed more fully below, the reactions contemplated in the present invention include reactions which are enantioselective, diastereoselective, and/or regioselective. An enantioselective reaction is a reaction which converts an achiral reactant to a chiral product enriched in one enantiomer. Enantioselectivity is generally quantified as "enantiomeric excess" (ee) defined as follows:

% Enantiomeric Excess $A$ $(ee)$=(% Enantiomer $A$)−(% Enantiomer $B$)

where A and B are the enantiomers formed. Additional terms that are used in conjunction with enatioselectivity include "optical purity" or "optical activity". An enantioselective reaction yields a product with an e.e. greater than zero. Preferred enantioselective reactions yield a product with an e.e. greater than 20%, more preferably greater than 50%, even more preferably greater than 70%, and most preferably greater than 80%.

A diastereoselective reaction converts a chiral reactant (which may be racemic or enantiomerically pure) to a product enriched in one diastereomer. If the chiral reactant is racemic, in the presence of a chiral non-racemic reagent or catalyst, one reactant enantiomer may react more slowly than the other. This class of reaction is termed a kinetic resolution, wherein the reactant enantiomers are resolved by differential reaction rate to yield both enantiomerically-enriched product and enantiomerically-enriched unreacted substrate. Kinetic resolution is usually achieved by the use of sufficient reagent to react with only one reactant enantiomer (i.e. one-half mole of reagent per mole of racemic substrate). Examples of catalytic reactions which have been used for kinetic resolution of racemic reactants include the Sharpless epoxidation and the Noyori hydrogenation.

A regioselective reaction is a reaction which occurs preferentially at one reactive center rather than another non-identical reactive center. For example, a regioselective reaction of an unsymmetrically substituted epoxide substrate would involve preferential reaction at one of the two epoxide ring carbons.

The term "non-racemic" with respect to the chiral catalyst, means a preparation of catalyst having greater than 50% of a given enantiomer, more preferably at least 75%. "Substantially non-racemic" refers to preparations of the catalyst which have greater than 90% ee for a given enantiomer of the catalyst, more preferably greater than 95% ee.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 of fewer. Likewise, preferred cycloalkyls have from 4–10 carbon atoms in their ring structure, and more preferably have 5, 6 or 7 carbons in the ring structure.

The terms "alkenyl" and "alkynyl" refer to unsaturated aliphatic groups analogous in length and possible substitution to the alkyls described above, but which contain at least one double or triple carbon-carbon bond, respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

The term "organometallic" refers to compounds comprising a metallic atom (such as mercury, zinc, lead, magnesium or lithium) or a metalloid atom (such as silicon, or tin) that is bonded directly to a carbon atom, such as methyl magnesium bromide, phenyl lithium, and phenyl-trimethyl-tin.

The terms "amine" and "amino" are art-recognized and refer to both unsubstituted and substituted amines, e.g., a moiety that can be represented by the general formula:

wherein $R_9$, $R_{10}$ and $R'_{10}$ each independently represent a group permitted by the rules of valence.

The term "acylamino" is art-recognized and refers to a moiety that can be represented by the general formula:

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The term "sulfonylamino" is art recognized and includes a moiety that can be represented by the general formula:

The term "sulfamoyl" is art-recognized and includes a moiety that can be represented by the general formula:

The term "sulfonyl", as used herein, refers to a moiety that can be represented by the general formula:

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

in which $R_{44}$ is selected from the group consisting of hydrogen, alkyl, alkenyl, alkynyl, cycloalkyl, heterocyclyl, aralkyl, or aryl.

The term "sulfate", as used herein, means a sulfonyl group, as defined above, attached to two hydroxy or alkoxy groups. Thus, in a preferred embodiment, a sulfate has the structure:

in which $R_{40}$ and $R_{41}$ are independently absent, a hydrogen, an alkyl, or an aryl. Furthermore, $R_{40}$ and $R_{41}$, taken together with the sulfonyl group and the oxygen atoms to which they are attached, may form a ring structure having from 5 to 10 members.

Analogous substitutions can be made to alkenyl and alkynyl groups to produce, for example, alkenylamines, alkynylamines, alkenylamides, alkynylamides, alkenylimines, alkynylimines, thioalkenyls, thioalkynyls, carbonyl-substituted alkenyls or alkynyls, alkenoxyls, alkynoxyls, metalloalkenyls and metalloalkynyls.

The term "aryl" as used herein includes 4-, 5-, 6- and 7-membered single-ring aromatic groups which may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycle". The aromatic ring can be substituted at one or more ring positions with such substituents as described above, as for example, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —(CH$_2$)$_m$—R$_7$, —CF$_3$, —CN, or the like.

The terms "heterocycle" or "heterocyclic group" refer to 4 to 10-membered ring structures, more preferably 5 to 7 membered rings, which ring structures include one to four heteroatoms. Heterocyclic groups include pyrrolidine, oxolane, thiolane, imidazole, oxazole, piperidine, piperazine, morpholine. The heterocyclic ring can be substituted at one or more positions with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —(CH$_2$)$_m$—R$_7$, —CF$_3$, —CN, or the like.

The terms "polycycle" or "polycyclic group" refer to two or more cyclic rings (e.g., cycloalkyls, cycloalkenyls, cycloalkynyls, aryls and/or heterocycles) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —(CH$_2$)$_m$—R$_7$, —CF$_3$, —CN, or the like.

The term "heteroatom" as used herein means an atom of any element other than carbon or hydrogen. Preferred heteroatoms are nitrogen, oxygen, sulfur, phosphorus and selenium.

For purposes of this invention, the chemical elements are identified in accordance with the Periodic Table of the Elements, CAS version, Handbook of Chemistry and Physics, 67th Ed., 1986–87, inside cover.

The terms ortho, meta and para apply to 1,2-, 1,3- and 1,4-disubstituted benzenes, respectively. For example, the names 1,2-dimethylbenzene and ortho-dimethylbenzene are synonymous.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms, represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Methods of the Invention

In certain embodiments, a method of the present invention is represented by Scheme 1:

wherein

X represents I, Br, Cl, alkylsulfonate, or arylsulfonate;

Ar represents optionally substituted aryl or heteroaryl;

catalyst consists essentially of a Group 8 atom or ion; and at least one carbene-containing ligand;

base represents a phosphate, carbonate, bicarbonate, fluoride, tertiary amine, or hydride;

R represents alkyl, alkenyl, cycloalkyl, aralkyl, aryl, heteroaryl, formyl, acyl, —CO$_2$alkyl, —CO$_2$aryl, —CO$_2$aralkyl, —N(R')acyl, —N(R')C(O)Oalkyl, —N(R')C(O)Oaryl, —N(R')C(O)Oaralkyl, —N=C(alkyl)$_2$, or —N=C(aryl)$_2$;

R' represents H, alkyl, cycloalkyl, aralkyl, aryl, heteroaryl, formyl, acyl, or amino;

R and R' taken together may represent =C(alkyl)$_2$, or =C(aryl)$_2$; and

R and R' are optionally connected by a covalent bond.

In certain embodiments, the methods of the present invention are represented by Scheme 1 and the attendant definitions, wherein X is Br or Cl.

In certain embodiments, the methods of the present invention are represented by Scheme 1 and the attendant definitions, wherein Ar represents optionally substituted phenyl.

In certain embodiments, the methods of the present invention are represented by Scheme 1 and the attendant definitions, wherein R' represents H, alkyl, cycloalkyl, aralkyl, aryl, or heteroaryl.

In certain embodiments, the methods of the present invention are represented by Scheme 1 and the attendant definitions, wherein the catalyst consists essentially of a palladium atom or ion; and at least one carbene-containing ligand.

In certain embodiments, the methods of the present invention are represented by Scheme 1 and the attendant definitions, wherein X is Br or Cl; and Ar represents optionally substituted phenyl.

In certain embodiments, the methods of the present invention are represented by Scheme 1 and the attendant definitions, wherein X is Br or Cl; Ar represents optionally substituted phenyl; and R' represents H, alkyl, cycloalkyl, aralkyl, aryl, or heteroaryl.

In certain embodiments, the methods of the present invention are represented by Scheme 1 and the attendant definitions, wherein X is Br or Cl; Ar represents optionally substituted phenyl; R' represents H, alkyl, cycloalkyl, aralkyl, aryl, or heteroaryl; and the catalyst consists essentially of a palladium atom or ion; and at least one carbene-containing ligand.

In certain embodiments, the methods of the present invention are represented by Scheme 1 and any of the aforementioned definitions, wherein the at least one carbene-containing ligand is represented by the following formula:

wherein $R^1$ and $R^2$ are independently selected from the group consisting of optionally substituted aryl; and $R^3$ and $R^4$ are independently selected from the group consisting of H and alkyl.

In certain embodiments, the methods of the present invention are represented by Scheme 1 and any of the aforementioned definitions, wherein the at least one carbene-containing ligand is represented by the following formula:

wherein $R^1$ and $R^2$ are independently selected from the group consisting of optionally substituted phenyl; and $R^3$ and $R^4$ are H.

In certain embodiments, the methods of the present invention are represented by Scheme 1 and any of the aforementioned definitions, wherein the at least one carbene-containing ligand is represented by the following formula:

wherein $R^1$ and $R^2$ are independently selected from the group consisting of optionally substituted aryl; and $R^3$ and $R^4$ are independently selected from the group consisting of H and alkyl.

In certain embodiments, the methods of the present invention are represented by Scheme 1 and any of the aforementioned definitions, wherein the at least one carbene-containing ligand is represented by the following formula:

wherein $R^1$ and $R^2$ are independently selected from the group consisting of optionally substituted phenyl; and $R^3$ and $R^4$ are H.

In certain embodiments, the methods of the present invention are represented by Scheme 1 and any of the aforementioned definitions, wherein base represents a phosphate.

In certain embodiments, the methods of the present invention are represented by Scheme 1 and any of the aforementioned definitions, wherein base represents potassium phosphate.

In certain embodiments, the methods of the present invention are represented by Scheme 1 and any of the aforementioned definitions, wherein R represents aryl or heteroaryl.

In certain embodiments, the methods of the present invention are represented by Scheme 1 and any of the aforementioned definitions, wherein R' represents H.

In certain embodiments, the methods of the present invention are represented by Scheme 1 and any of the aforementioned definitions, wherein R represents aryl or heteroaryl; and R' represents H.

In certain embodiments, the methods of the present invention are represented by Scheme 1 and any of the aforementioned definitions, wherein the method is practiced at a temperature less than about 150 C.

In certain embodiments, the methods of the present invention are represented by Scheme 1 and any of the aforementioned definitions, wherein the method is practiced at a temperature in the range from about 90 C to about 110 C.

In certain embodiments, the methods of the present invention are represented by Scheme 1 and any of the aforementioned definitions, wherein the method is practiced at about 100 C.

Reaction Conditions

The methods of the present invention may be performed under a wide range of conditions, though it will be understood that the solvents and temperature ranges recited herein are not limitative and only correspond to a preferred mode of the process of the invention.

In general, it will be desirable that reactions are run using mild conditions which will not adversely affect the reactants, the catalyst, or the product. For example, the reaction temperature influences the speed of the reaction, as well as the stability of the reactants, products and catalyst.

In general, the subject reactions are carried out in a liquid reaction medium. The reactions may be run without addition of solvent. Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, xylene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents.

The invention also contemplates reaction in a biphasic mixture of solvents, in an emulsion or suspension, or reaction in a lipid vesicle or bilayer. In certain embodiments, it may be preferred to perform the catalyzed reactions in the solid phase with one of the reactants anchored to a solid support.

In certain embodiments it is preferable to perform the reactions under an inert atmosphere of a gas such as nitrogen or argon.

The reaction processes of the present invention can be conducted in continuous, semi-continuous or batch fashion and may involve a liquid recycle operation as desired. The processes of this invention are preferably conducted in batch fashion. Likewise, the manner or order of addition of the reaction ingredients, catalyst and solvent are also not generally critical to the success of the reaction, and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the metal catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, one or more of the reactants or the catalyst can be immobilized by attachment to or incorporation into a polymer or other insoluble matrix.

Subsequent Transformations

A product synthesized by a method of the present invention may be either an end-product or an intermediate in a synthesis scheme. In cases where the product synthesized by a method of the present invention is an intermediate, the product may be subjected to one or more additional transformations to yield the desired end-product. The set of additional transformations contemplated comprises isomerizations, hydrolyses, oxidations, reductions, additions, eliminations, olefinations, functional group interconversions, transition metal-mediated reactions, transition metal-catalyzed reactions, bond-forming reactions, cleavage reactions, fragmentation reactions, thermal reactions, photochemical reactions, cycloadditions, sigmatropic rearrangements, electrocyclic reactions, chemoselective reactions, regioselective reactions, stereoselective reactions, diastereoselective reactions, enantioselective reactions, and kinetic resolutions. The invention expressly comprises use of a method of the present invention as a step—either initial, intermediate or final—in the synthesis of known or new pharmaceuticals, e.g., antivirals, antibiotics, and analgesics.

Combinatorial Libraries

The subject methods of the present invention readily lend themselves to the creation of combinatorial libraries of compounds for the screening of pharmaceutical, agrochemical or other biological or medical activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules. See, for example, Blondelle et al. (1995) Trends Anal. Chem. 14:83; the Affymax U.S. Pat. Nos. 5,359,115 and 5,362,899: the Ellman U.S. Pat. No. 5,288,514: the Still et al. PCT publication WO 94/08051; Chen et al. (1994) JACS 116:2661: Kerr et al. (1993) JACS 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay.

EXEMPLIFICATION

The invention now being generally described, it will be more readily understood by reference to the following examples which are included merely for purposes of illustration of certain aspects and embodiments of the present invention, and are not intended to limit the invention.

Example 1

Preparation of N-(2-Nitrophenyl)-p-anisidine (1a)

Figure 1:
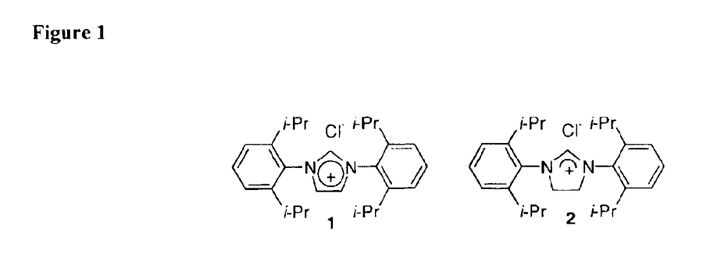
FIG. 1 depicts two embodiments of the carbene ligands used in the methods of the present invention.
Figure 2:
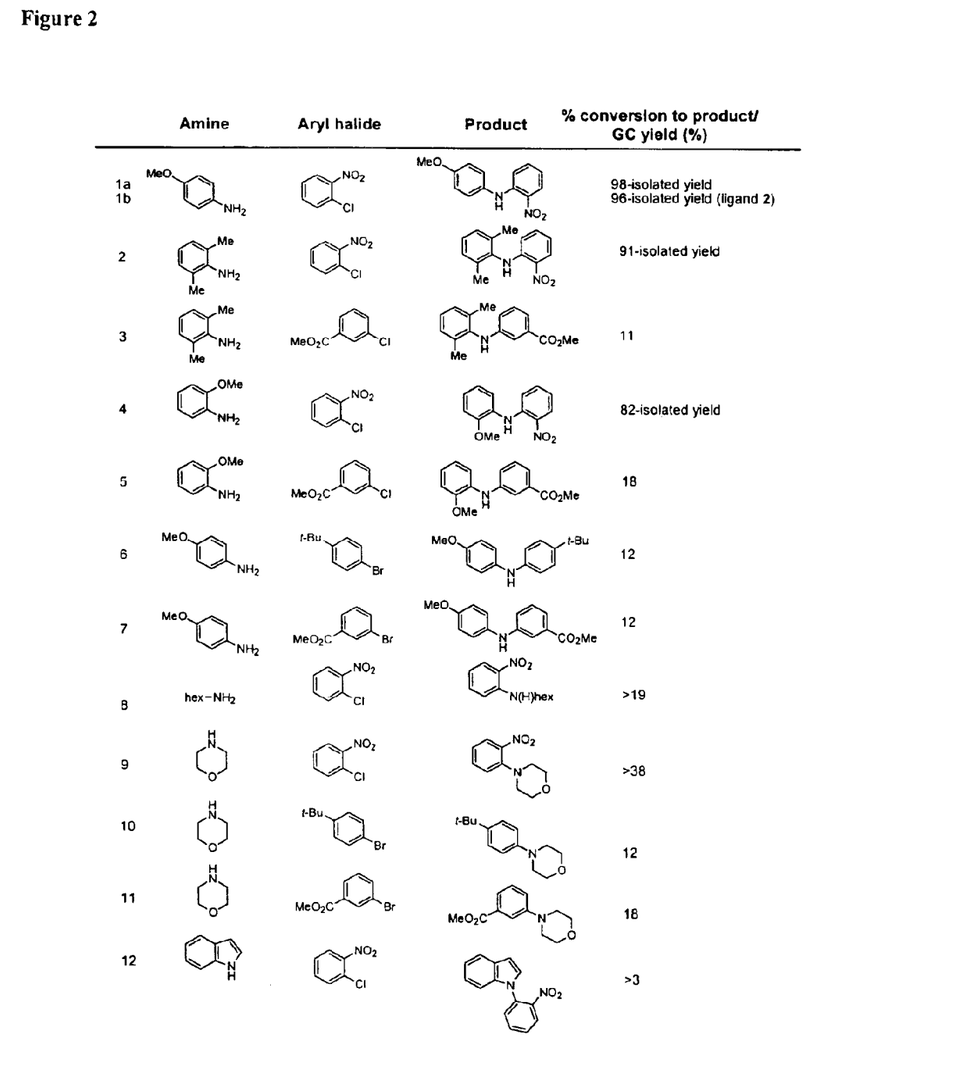
FIG. 2 tabulates the embodiments of the methods of the present invention described in Examples 1–13.

$Pd_2(dba)_3$ (4.6 mg, 0.005 mmol, 1 mol % Pd), ligand 1 (see FIG. 1) (8.4 mg, 0.02 mmol) and NaOt-Bu (2 mg, 0.02 mmol) were stirred in 1 mL DME (anhy). After 10 minutes, the solution was added to a test tube containing (under an Argon atmosphere) $K_3PO_4$ (297 mg, 1.4 mmol), 2-nitrochlorobenzene (158 mg, 1.0 mmol), and p-anisidine (148 mg, 1.2 mmol). The test tube was capped and heated at 100° C. for 35 hours. The reaction mixture was cooled to r.t., diluted with ether and dodecane was added as an internal standard. The reaction mixture was purified by column chromatography (10% EtOAc/hexanes) to yield 238 mg (98% yield) of the product.

Example 2

Preparation of N-(2-Nitrophenyl)-p-anisidine (1b)

Pd(dba)$_2$ (5.8 mg, 0.01 mmol, 1 mol % Pd), ligand 2 (see FIG. 1) (4.2 mg, 0.01 mmol) and NaOt-Bu (1 mg, 0.01 mmol) were stirred in 1 mL DME (anhy). After 10 minutes, the solution was added to a test tube containing (under an Argon atmosphere) K$_3$PO$_4$ (297 mg, 1.4 mmol), 2-nitrochlorobenzene (158 mg, 1.0 mmol), and p-anisidine (148 mg, 1.2 mmol). The test tube was capped and heated at 100° C. for 35 hours. The reaction mixture was cooled to r.t., diluted with ether and dodecane was added as an internal standard. The reaction mixture was purified by column chromatography (10% EtOAc/hexanes) to yield 234 mg (96% yield) of the product.

Example 3

Preparation of N-(2,6-Dimethylphenyl)-2-nitroaniline (2)

A solution of ligand 1 (see FIG. 1) [42 mg, 0.1 mmol (8.4 mg, 0.02 mmol, 4 mol % per reaction)] and NaOt-Bu [10 mg, 0.1 mmol (2 mg, 0.02 mmol, 4 mol % per reaction)] were stirred in 5 mL DME (anhy). After 10 minutes, 1 mL of the solution was added via syringe to a test tube containing (under an Argon atmosphere) Pd$_2$(dba)$_3$ (4.6 mg, 0.005 mmol, 2 mol % Pd), K$_3$PO$_4$ (148 mg, 0.7 mmol), 2-chloronitrobenzene (79 mg, 0.5 mmol), and 2,6-dimethylaniline (74 μL, 0.6 mmol). The test tube was capped (with a proper cap-no rubber septa) and heated at 100° C. for 18 hours. The reaction mixture was allowed to cool to r.t., diluted with ether and dodecane was added as an internal standard. The reaction mixture was purified by column chromatography (5% EtOAc/hexanes) to yield 110 mg (91% yield) of the product.

Example 4

Preparation of Methyl-3-(N-2,6-Dimethylphenyl amino) benzoate (3)

A solution of ligand 1 (see FIG. 1) [42 mg, 0.1 mmol (8.4 mg, 0.02 mmol, 4 mol % per reaction)] and NaOt-Bu [10 mg, 0.1 mmol (2 mg, 0.02 mmol, 4 mol % per reaction)] were stirred in 5 mL DME (anhy). After 10 minutes, 1 mL of the solution was added via syringe to a test tube containing (under an Argon atmosphere) Pd$_2$(dba)$_3$ (4.6 mg, 0.005 mmol, 2 mol % Pd), K$_3$PO$_4$ (148 mg, 0.7 mmol), methyl-3-chlorobenzoate (70 μL, 0.5 mmol), and 2,6-dimethylanili (74 μL, 0.6 mmol). The test tube was capped (with a proper cap-no rubber septa) and heated at 100° C. for 18 hours. The reaction mixture was allowed to cool to r.t., diluted with ether and dodecane was added as an internal standard. The reaction mixture was purified by preparatory TLC (EtOAc/hexanes as the eluent) to yield 6 mg of the desired product (which was used for calibration with the internal standard). The GC yield was calculated to be 11%.

Example 5

Preparation of N-(2-methoxyphenyl)-2-nitroaniline (4)

A solution of ligand 1 (see FIG. 1) [42 mg, 0.1 mmol (8.4 mg, 0.02 mmol, 4 mol % per reaction)] and NaOt-Bu [10 mg, 0.1 mmol (2 mg, 0.02 mmol, 4 mol % per reaction)] were stirred in 5 mL DME (anhy). After 10 minutes, 1 mL of the solution was added via syringe to a test tube containing (under an Argon atmosphere) Pd$_2$(dba)$_3$ (4.6 mg, 0.005 mmol, 2 mol % Pd), K$_3$PO$_4$ (148 mg, 0.7 mmol), 2-chloronitrobenzene (79 mg, 0.5 mmol), and o-anisidine (68 μL, 0.6 mmol). The test tube was capped (with a proper cap-no rubber septa) and heated at 100° C. for 18 hours. The reaction mixture was allowed to cool to r.t., diluted with ether and dodecane was added as an internal standard (the consumption of the aryl chloride was incomplete). The reaction mixture was purified by column chromatography (5% EtOAc/hexanes) to yield 100 mg (82% yield) of the product.

Example 6

Preparation of Methyl-3-(N-2-methoxyphenyl amino) benzoate (5)

A solution of ligand 1 (see FIG. 1) [42 mg, 0.1 mmol (8.4 mg, 0.02 mmol, 4 mol % per reaction)] and NaOt-Bu [10 mg, 0.1 mmol (2 mg, 0.02 mmol, 4 mol % per reaction)] were stirred in 5 mL DME (anhy). After 10 minutes, 1 mL of the solution was added via syringe to a test tube containing (under an Argon atmosphere) Pd$_2$(dba)$_3$ (4.6 mg, 0.005 mmol, 2 mol % Pd), K$_3$PO$_4$ (148 mg, 0.7 mmol), methyl-3-chlorobenzoate (70 μL, 0.5 mmol), and o-anisidine (68 μL, 0.6 mmol). The test tube was capped (with a proper cap-no rubber septa) and heated at 100° C. for 18 hours. The reaction mixture was allowed to cool to r.t., diluted with ether and dodecane was added as an internal standard. The reaction mixture was purified by column chromatography (5% EtOAc/hexanes as the eluent) to yield 20 mg of the desired product which was ~93% pure. This was purified further by preparatory TLC (EtOAc/hexanes as the eluent) to yield 12 mg of the desired product (which was used for calibration with the internal standard). The GC yield was calculated to be 18%.

Example 7

Preparation of N-(4-tert-butylphenyl)-p-anisidine (6)

A solution of Pd$_2$(dba)$_3$ [92 mg, 0.1 mmol (4.6 mg, 0.005 mmol, 2 mol % Pd per reaction)], ligand 1 (see FIG. 1) [168 mg, 0.4 mmol (8.4 mg, 0.02 mmol, 4 mol % per reaction)] and NaOt-Bu [40 mg, 0.4 mmol (2 mg, 0.02 mmol, 4 mol % per reaction)] were stirred in 10 mL DME (anhy). After 10 minutes, 0.5 mL of the solution was added via syringe to a test tube containing (under an Argon atmosphere) K$_3$PO$_4$ (148 mg, 0.7 mmol), 1-bromo-4-tert-butylbenzene (86 μL, 0.5 mmol), and p-anisidine (74 mg, 0.6 mmol). The test tube was capped (with a proper cap-no rubber septa) and heated at 100° C. for 18 hours. The reaction mixture was allowed to cool to r.t., diluted with ether and dodecane was added as an internal standard. The reaction mixture was purified by preparatory TLC (EtOAc/hexanes as the eluent) to yield 7 mg of the desired product (which was used for calibration with the internal standard). The GC yield was calculated to be 12%.

Example 8

Preparation of Methyl-3-(N-p-methoxylphenyl amino)benzoate (7)

A solution of Pd$_2$(dba)$_3$ [92 mg, 0.1 mmol (4.6 mg, 0.005 mmol, 2 mol % Pd per reaction)], ligand 1 (see FIG. 1) [168 mg, 0.4 mmol (8.4 mg, 0.02 mmol, 4 mol % per reaction)] and NaOt-Bu [40 mg, 0.4 mmol (2 mg, 0.02 mmol, 4 mol % per reaction)] were stirred in 10 mL DME (anhy). After 10 minutes, 0.5 mL of the solution was added via syringe to a test tube containing (under an Argon atmosphere) $K_3PO_4$ (148 mg, 0.7 mmol), methyl-3-bromo-benzoate (107 mg, 0.5 mmol), and p-anisidine (74 mg, 0.6 mmol). The test tube was capped (with a proper cap-no rubber septa) and heated at 100° C. for 18 hours. The reaction mixture was allowed to cool to r.t., diluted with ether and dodecane was added as an internal standard. The reaction mixture was purified by preparatory TLC (EtOAc/hexanes as the eluent) to yield 6 mg of the desired product (which was used for calibration with the internal standard). The GC yield was calculated to be 12%.

Example 9

Preparation of N-Hexyl-2-nitroaniline (8)

A solution of $Pd_2(dba)_3$ [92 mg, 0.1 mmol (4.6 mg, 0.005 mmol, 2 mol % Pd per reaction)], ligand 1 (see FIG. 1) [168 mg, 0.4 mmol (8.4 mg, 0.02 mmol, 4 mol % per reaction)] and NaOt-Bu [40 mg, 0.4 mmol (2 mg, 0.02 mmol, 4 mol % per reaction)] were stirred in 10 mL DME (anhy). After 10 minutes, 0.5 mL of the solution was added via syringe to a test tube containing (under an Argon atmosphere) $K_3PO_4$ (148 mg, 0.7 mmol), 2-chloronitrobenzene (79 mg, 0.5 mmol), and hexylamine (79 μL, 0.6 mmol). The test tube was capped (with a proper cap-no rubber septa) and heated at 100° C. for 18 hours. The reaction mixture was allowed to cool to r.t., diluted with ether and dodecane was added as an internal standard. The reaction mixture was purified by preparatory TLC (EtOAc/hexanes as the eluent) to yield 3 mg of the desired product (which was used for calibration with the internal standard). The GC yield was calculated to be 19%.

Example 10

Preparation of N-(2-nitrophenyl) morpholine (9)

A solution of $Pd_2(dba)_3$ [92 mg, 0.1 mmol (4.6 mg, 0.005 mmol, 2 mol % Pd per reaction)], ligand 1 (see FIG. 1) [168 mg, 0.4 mmol (8.4 mg, 0.02 mmol, 4 mol % per reaction)] and NaOt-Bu [40 mg, 0.4 mmol (2 mg, 0.02 mmol, 4 mol % per reaction)] were stirred in 10 mL DME (anhy). After 10 minutes, 0.5 mL of the solution was added via syringe to a test tube containing (under an Argon atmosphere) $K_3PO_4$ (148 mg, 0.7 mmol), 2-chloronitrobenzene (79 mg, 0.5 mmol), and morpholine (52 μL, 0.6 mmol). The test tube was capped (with a proper cap-no rubber septa) and heated at 100° C. for 18 hours. The reaction mixture was allowed to cool to r.t., diluted with ether and dodecane was added as an internal standard. The reaction mixture was purified by preparatory TLC (EtOAc/hexanes as the eluent) to yield 10 mg of the desired product (which was used for calibration with the internal standard). The GC yield was calculated to be 38%.

Example 11

Preparation of N-(4-t-Butylphenyl) morpholine (10)

A solution of $Pd_2(dba)_3$ [92 mg, 0.1 mmol (4.6 mg, 0.005 mmol, 2 mol % Pd per reaction)], ligand 1 (see FIG. 1) [168 mg, 0.4 mmol (8.4 mg, 0.02 mmol, 4 mol % per reaction)] and NaOt-Bu [40 mg, 0.4 mmol (2 mg, 0.02 mmol, 4 mol % per reaction)] were stirred in 10 mL DME (anhy). After 10 minutes, 0.5 mL of the solution was added via syringe to a test tube containing (under an Argon atmosphere) $K_3PO_4$ (148 mg, 0.7 mmol), 1-bromo-4-tert-butylbenzene (86 μL, 0.5 mmol), and morpholine (52 μL, 0.6 mmol). The test tube was capped (with a proper cap-no rubber septa) and heated at 100° C. for 18 hours. The reaction mixture was allowed to cool to r.t., diluted with ether and dodecane was added as an internal standard. The GC yield was calculated to be 12%.

Example 12

Preparation of Methyl-3-(morpholino)benzoate (11)

A solution of $Pd_2(dba)_3$ [92 mg, 0.1 mmol (4.6 mg, 0.005 mmol, 2 mol % Pd per reaction)], ligand 1 (see FIG. 1) [168 mg, 0.4 mmol (8.4 mg, 0.02 mmol, 4 mol % per reaction)] and NaOt-Bu [40 mg, 0.4 mmol (2 mg, 0.02 mmol, 4 mol % per reaction)] were stirred in 10 mL DME (anhy). After 10 minutes, 0.5 mL of the solution was added via syringe to a test tube containing (under an Argon atmosphere) $K_3PO_4$ (148 mg, 0.7 mmol), methyl-3-bromo-benzoate (107 mg, 0.5 mmol), and morpholine (52 μL, 0.6 mmol). The test tube was capped (with a proper cap-no rubber septa) and heated at 100° C. for 18 hours. The reaction mixture was allowed to cool to r.t., diluted with ether and dodecane was added as an internal standard. The reaction mixture was purified by preparatory TLC (EtOAc/hexanes as the eluent) to yield 6 mg of the desired product (which was used for calibration with the internal standard). The GC yield was calculated to be 18%.

Example 13

Preparation of N-(2-nitrophenyl) indole (12)

A solution of $Pd_2(dba)_3$ [92 mg, 0.1 mmol (4.6 mg, 0.005 mmol, 2 mol % Pd per reaction)], ligand 1 (see FIG. 1) [168 mg, 0.4 mmol (8.4 mg, 0.02 mmol, 4 mol % per reaction)] and NaOt-Bu [40 mg, 0.4 mmol (2 mg, 0.02 mmol, 4 mol % per reaction)] were stirred in 10 mL DME (anhy). After 10 minutes, 0.5 mL of the solution was added via syringe to a test tube containing (under an Argon atmosphere) $K_3PO_4$ (148 mg, 0.7 mmol), 2-chloronitrobenzene (79 mg, 0.5 mmol), and indole (70 mg, 0.6 mmol). The test tube was capped (with a proper cap-no rubber septa) and heated at 100° C. for 18 hours. The reaction mixture was allowed to cool to r.t., diluted with ether and dodecane was added as an internal standard. The GC yield was calculated to be 3%.

Incorporation by Reference

All of the patents and publications cited in the Specification are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:
1. A method represented by Scheme 1:

Scheme 1 wherein
X represents I, Br, Cl, alkylsulfonate, or arylsulfonate;
Ar represents optionally substituted aryl or heteroaryl;
catalyst consists essentially of a Group 8 atom or ion; and at least one carbene-containing ligand;
base represents a phosphate, carbonate, bicarbonate, fluoride, tertiary amine, or hydride;
R represents alkyl, alkenyl, cycloalkyl, aralkyl, aryl, heteroaryl, formyl, acyl, —$CO_2$alkyl, —$CO_2$aryl, —$CO_2$aralkyl, —N(R')acyl, —N(R')C(O)Oalkyl, —N(R')C(O)Oaryl, —N(R')C(O)Oaralkyl, —N=C(alkyl)$_2$, or —N=C(aryl)$_2$;
R' represents H, alkyl, cycloalkyl, aralkyl, aryl, heteroaryl, formyl, acyl, or amino;
R and R' taken together may represent C(alkyl)$_2$, or =C(aryl)$_2$; and
R and R' are optionally connected by a covalent bond to form a cyclic structure which incorporates the amine nitrogen.
2. The method of claim 1, wherein X is Br or Cl.
3. The method of claim 1, wherein Ar represents optionally substituted phenyl.
4. The method of claim 1, wherein R' represents H, alkyl, cycloalkyl, aralkyl, aryl, or heteroaryl.
5. The method of claim 1, wherein the catalyst consists essentially of a palladium atom or ion and at least one carbene-containing ligand.
6. The method of claim 1, wherein X is Br or Cl; and Ar represents optionally substituted phenyl.
7. The method of claim 1, wherein X is Br or Cl; Ar represents optionally substituted phenyl; and R' represents H, alkyl, cycloalkyl, aralkyl, aryl, or heteroaryl.
8. The method of claim 1, wherein X is Br or Cl; Ar represents optionally substituted phenyl; R' represents H, alkyl, cycloalkyl, aralkyl, aryl, or heteroaryl; and the catalyst consists essentially of a palladium atom or ion and at least one carbene-containing ligand.
9. The method of claim 1, 2, 3, 4, 5, 6, 7, or 8, wherein the at least one carbene-containing ligand is represented by the following formula:

wherein $R^1$ and $R^2$ are independently selected from the group consisting of optionally substituted aryl; and $R^3$ and $R^4$ are independently selected from the group consisting of H and alkyl.
10. The method of claim 1, 2, 3, 4, 5, 6, 7, or 8, wherein the at least one carbene-containing ligand is represented by the following formula:

wherein $R^1$ and $R^2$ are independently selected from the group consisting of optionally substituted phenyl; and $R^3$ and $R^4$ are H.
11. The method of claim 1, 2, 3, 4, 5, 6, 7, or 8, wherein the at least one carbene-containing ligand is represented by the following formula:

wherein $R^1$ and $R^2$ are independently selected from the group consisting of optionally substituted aryl; and $R^3$ and $R^4$ are independently selected from the group consisting of H and alkyl.
12. The method of claim 1, 2, 3, 4, 5, 6, 7, or 8, wherein the at least one carbene-containing ligand is represented by the following formula:

wherein $R^1$ and $R^2$ are independently selected from the group consisting of optionally substituted phenyl; and $R^3$ and $R^4$ are H.
13. The method of claim 1, 2, 3, 4, 5, 6, 7, or 8, wherein base represents a phosphate.
14. The method of claim 1, 2, 3, 4, 5, 6, 7, or 8, wherein base represents potassium phosphate.
15. The method of claim 1, 2, 3, 4, 5, 6, 7, or 8, wherein R represents aryl or heteroaryl.
16. The method of claim 1, 2, 3, 4, 5, 6, 7, or 8, wherein R' represents H.
17. The method of claim 1, 2, 3, 4, 5, 6, 7, or 8, wherein R represents aryl or heteroaryl; and R' represents H.
18. The method of claim 1, 2, 3, 4, 5, 6, 7, or 8, wherein the method is practiced at a temperature less than about 150 C.
19. The method of claim 1, 2, 3, 4, 5, 6, 7, or 8, wherein the method is practiced at a temperature in the range from about 90 C to about 110 C.
20. The method of claim 1, 2, 3, 4, 5, 6, 7, or 8, wherein the method is practiced at about 100 C.

* * * * *

UNITED STATES PATENT AND TRADEMARK OFFICE
CERTIFICATE OF CORRECTION

PATENT NO. : 6,888,029 B2
APPLICATION NO. : 10/349198
DATED : May 3, 2005
INVENTOR(S) : Stephen L. Buchwald et al.

Page 1 of 1

It is certified that error appears in the above-identified patent and that said Letters Patent is hereby corrected as shown below:

Column 1, lines 12-14, replace:

"The invention was made with support provided by the National Institutes of Health; therefore, the government has certain rights in the invention."

with

--This invention was made with government support under Grant No. R01 GM034917, awarded by the National Institute of Health and under Grant No. CHE9000482, awarded by the National Science Foundation. The government has certain rights in this invention.--

Signed and Sealed this
Tenth Day of May, 2011

David J. Kappos
*Director of the United States Patent and Trademark Office*